(12) United States Patent
Kawahara et al.

(10) Patent No.: US 7,961,842 B2
(45) Date of Patent: Jun. 14, 2011

(54) X-RAY FLUORESCENCE SPECTROMETER AND PROGRAM USED THEREIN

(75) Inventors: Naoki Kawahara, Takatsuki (JP); Shinya Hara, Takatsuki (JP)

(73) Assignee: Rigaku Corporation, Tokyo (JP)

( * ) Notice: Subject to any disclaimer, the term of this patent is extended or adjusted under 35 U.S.C. 154(b) by 221 days.

(21) Appl. No.: 11/910,510

(22) PCT Filed: Dec. 8, 2005

(86) PCT No.: PCT/JP2005/022552
§ 371 (c)(1),
(2), (4) Date: Oct. 2, 2007

(87) PCT Pub. No.: WO2006/112084
PCT Pub. Date: Oct. 26, 2006

(65) Prior Publication Data
US 2009/0041184 A1    Feb. 12, 2009

(30) Foreign Application Priority Data
Apr. 6, 2005 (JP) .................. 2005-109503

(51) Int. Cl.
*G01N 23/223* (2006.01)
(52) U.S. Cl. .......................... 378/45; 378/44
(58) Field of Classification Search ............ 378/44, 378/45
See application file for complete search history.

(56) References Cited

U.S. PATENT DOCUMENTS

| | | | |
|---|---|---|---|
| 6,292,532 B1 * | 9/2001 | Kawahara et al. | 378/49 |
| 6,385,281 B1 | 5/2002 | Ozawa et al. | |
| 6,668,038 B2 * | 12/2003 | Kataoka et al. | 378/45 |
| 7,187,751 B2 * | 3/2007 | Kawahara et al. | 378/45 |
| 2003/0142781 A1 | 7/2003 | Kawahara et al. | |

FOREIGN PATENT DOCUMENTS

| | | |
|---|---|---|
| JP | 2001-83109 A | 3/2001 |
| JP | 2003-297891 A | 10/2003 |
| JP | 2006-71311 A | 3/2006 |

OTHER PUBLICATIONS

International Preliminary Report on Patentability, dated Oct. 18, 2007.
Japanese Patent Office Action for Application No. 2005-109503, dated Feb. 27, 2007.
D. K. G. de Boer, "Angular Dependence of X-Ray Fluorescence Intensitites", X-Ray Spectrometry, 1989, pp. 119-129, vol. 18.
Yoshihiro Mori, et al, "A Depth Profile Fitting Model for a Commercial Total Reflection X-Ray Fluorescence Spectrometer", Spectrochimica Acta Part B, 1997, pp. 823-828, vol. 52.
"X-Ray Fluorescence Spectrometer ZSX Primus II" The Rigaku Journal, May 2005, pp. 42-45, vol. 22, No. 1.
Chinese Office Action, dated Sep. 16, 2010, for Chinese Patent Application No. 200580049351.0.
Chinese Office Action dated Jan. 12, 2011 for Chinese Patent Application No. 200580049351.0.

* cited by examiner

*Primary Examiner* — Hoon Song
*Assistant Examiner* — Mona M Sanei
(74) *Attorney, Agent, or Firm* — Sughrue Mion, PLLC

(57) ABSTRACT

An X-ray fluorescence spectrometer which includes a calculating device (10) operable to calculate the theoretical intensity of secondary X-rays (6), emanated from each of elements contained in a sample (13), based on the assumed composition and then to successively approximately modify and calculate the assumed composition so that the theoretical intensity and the converted and measured intensity, which have been detected by a detecting device (9) and then converted in a theoretical intensity scale, can match with each other, to thereby calculate the composition of the sample (13). The calculating device (10), when calculating the theoretical intensity, performs a simulation to determine the theoretical intensity of the secondary X-rays (6) for each of optical paths, using the size of the sample (13), and the intensity and the incident angle ($\phi$) of primary X-rays (2) impinged upon various areas of the sample surface (13a) as parameters.

5 Claims, 4 Drawing Sheets

X-RAY FLUORESCENCE SPECTROMETER AND PROGRAM USED THEREIN

BACKGROUND OF THE INVENTION

The present invention relates to an X-ray fluorescence spectrometer for analyzing the composition of and the area density of a sample based on the FP method and a program for use therein.

The X-ray fluorescence spectrometer has hitherto been well known, which analyzes the composition of and the area density of a sample by the utilization of the fundamental parameter method (hereinafter referred to as "FP method"). According to the FP method, based on the assumed composition, the assumed concentrations of elements in other words, the theoretical intensity of the secondary X-rays emanated from elements contained in the sample is calculated and the assumed composition is successively approximately modified and calculated so that the calculated theoretical intensity and the converted and measured intensity, which has been detected by a detecting device and then converted in a theoretical intensity scale, can match with each other, thereby calculating the concentration of each of the elements contained in the sample, the composition of the sample in other words. In calculating the theoretical intensity referred to above, the computation model is employed, in which the sample that is infinitely large in size is uniformly irradiated with parallel primary X-rays and secondary X-rays emanated from a portion thereof are observed.

In practice, however, not only the size of the sample, but the radiation area of primary X-rays is finite and the incident angle of primary X-rays changes with the position of incidence thereof. Accordingly, the intensity of the secondary X-rays emanating actually from the sample does not completely match with the intensity of the secondary X-rays emanated in the previously discussed computation model. While this is referred to as the geometry effect, the analysis will not result in presentation of a sufficiently accurate composition of the sample unless the theoretical intensity is computed with the geometry effect taken sufficiently into consideration in conformity with the reality.

In view of the foregoing, in order to enable computation of the theoretical intensity with the geometry effect taken into consideration, a software application, which is tradenamed "UniQuant", is presented from Omega Data System. According to this software application, the theoretical intensity is computed with the use of the sensitivity curve, which has been determined in the direction of depth of the sample by systematically changing the thickness thereof.

However, the sensitivity curve in the direction of depth varies depending on the secondary X-rays and the composition of an object to be analyzed, proper application of this conventional technique to various kinds of samples requires a number of sensitivity curves to be determined ahead of time and this is not realistic.

SUMMARY OF THE INVENTION

The present invention has been devised in the light of the presence of the foregoing problems and is intended to provide an X-ray fluorescence spectrometer, and a program used therein, for analyzing the composition of and the area density of a sample according to the FP method, in which with respect to various kinds of samples, the theoretical intensity can be computed simply and with the geometry effect taken sufficiently into consideration in conformity with the reality and the samples can be quantitatively analyzed with sufficient accuracy.

In order to accomplish the foregoing object of the present invention, one aspect of the present invention provides an X-ray fluorescence spectrometer which includes an X-ray source for irradiating primary X-rays towards a sample; a detecting device for measuring the intensity of secondary X-rays emanating from the sample; and a calculating device operable to calculate the theoretical intensity of the secondary X-rays, emanated from each of elements contained in the sample, based on the assumed composition and then to successively approximately modify and calculate the assumed composition so that the calculated theoretical intensity and the converted and measured intensity, which have been detected by the detecting device and then converted in a theoretical intensity scale, can match with each other, to thereby calculate the composition of the sample; characterized in that the calculating device, when calculating the theoretical intensity, performs a simulation to determine the theoretical intensity of the secondary X-rays for each of optical paths, using the size of the sample, and the intensity and the incident angle of primary X-rays impinged upon various areas of the sample surface as parameters.

With the X-ray fluorescence spectrometer according to the first aspect of the present invention, since in calculating the theoretical intensity, the simulated calculation to determine the theoretical intensity of the secondary X-rays for each optical path is carried out using the size of the sample, the incident angle and the intensity of primary X-rays impinged upon various position of the sample surface as parameters, there is no need to prepare a plurality of sensitivity curves ahead of time and, with respect to various samples, the theoretical intensity can be calculated conveniently with the geometry effect sufficiently taken into consideration in conformity with the reality and the samples can be quantitatively analyzed sufficiently accurately. It is to be noted that the total length of time required to calculate the composition of the sample may be prolonged as compared with that in the conventional case, but can fall within the practically sufficient range.

In the X-ray fluorescence spectrometer according to the first aspect of the present invention, the calculating device preferably calculates the theoretical intensity simultaneously with respect to a plurality of the assumed composition. According to this preferred construction, the total length of time required to complete the calculation can be reduced.

Also, in the X-ray fluorescence spectrometer according to the first aspect of the present invention, the calculating device preferably makes use of a distribution of incident angles or a distribution of scattering angles of primary X-rays on the sample surface, which has been predetermined ahead of time. Since the distribution of incident angles or the distribution of scattering angles of primary X-rays on the sample surface do not generally change unless the X-ray source is changed, in this preferred construction they are, after having been determined ahead of time, used in the calculation of the theoretical intensity. According to this, since the length of time required to accomplish the calculation of the theoretical intensity, the total length of time in accomplishing the calculation can also be reduced. It is also to be noted that since the distributions of the incident angles and the scattering angles at the sample surface do not generally change with change of the sample, there is no need to prepare a number of distributions such as a number of sensitivity curves required in the conventional art.

Furthermore, in the X-ray fluorescence spectrometer according to the first aspect of the present invention, a sample container provided with a scale for measuring the height of the sample surface may be preferably employed. Since the incident angle and the intensity of primary X-rays irradiated on each position of the sample surface as the parameter referred to previously changes with the height of the sample surface relative to the X-ray source and, therefore, the height of the sample surface must be known. In this preferred construction, since the sample container is provided with the scale for measuring the height of the sample surface, measurement and adjustment of the height of the sample surface can be easily accomplished.

The present invention in accordance with a second aspect thereof provides a program for enabling a computer included in the X-ray fluorescence spectrometer according to the first aspect of the present invention, to function as the calculating device. Even with this program according to the second aspect of the present invention, functions and effects similar to those afforded by the X-ray fluorescence spectrometer according to the first aspect of the present invention can be obtained.

BRIEF DESCRIPTION OF THE DRAWINGS

In any event, the present invention will become more clearly understood from the following description of preferred embodiments thereof, when taken in conjunction with the accompanying drawings. However, the embodiments and the drawings are given only for the purpose of illustration and explanation, and are not to be taken as limiting the scope of the present invention in any way whatsoever, which scope is to be determined by the appended claims. In the accompanying drawings, like reference numerals are used to denote like parts throughout the several views, and:

DESCRIPTION OF THE PREFERRED EMBODIMENTS

Figure 1:
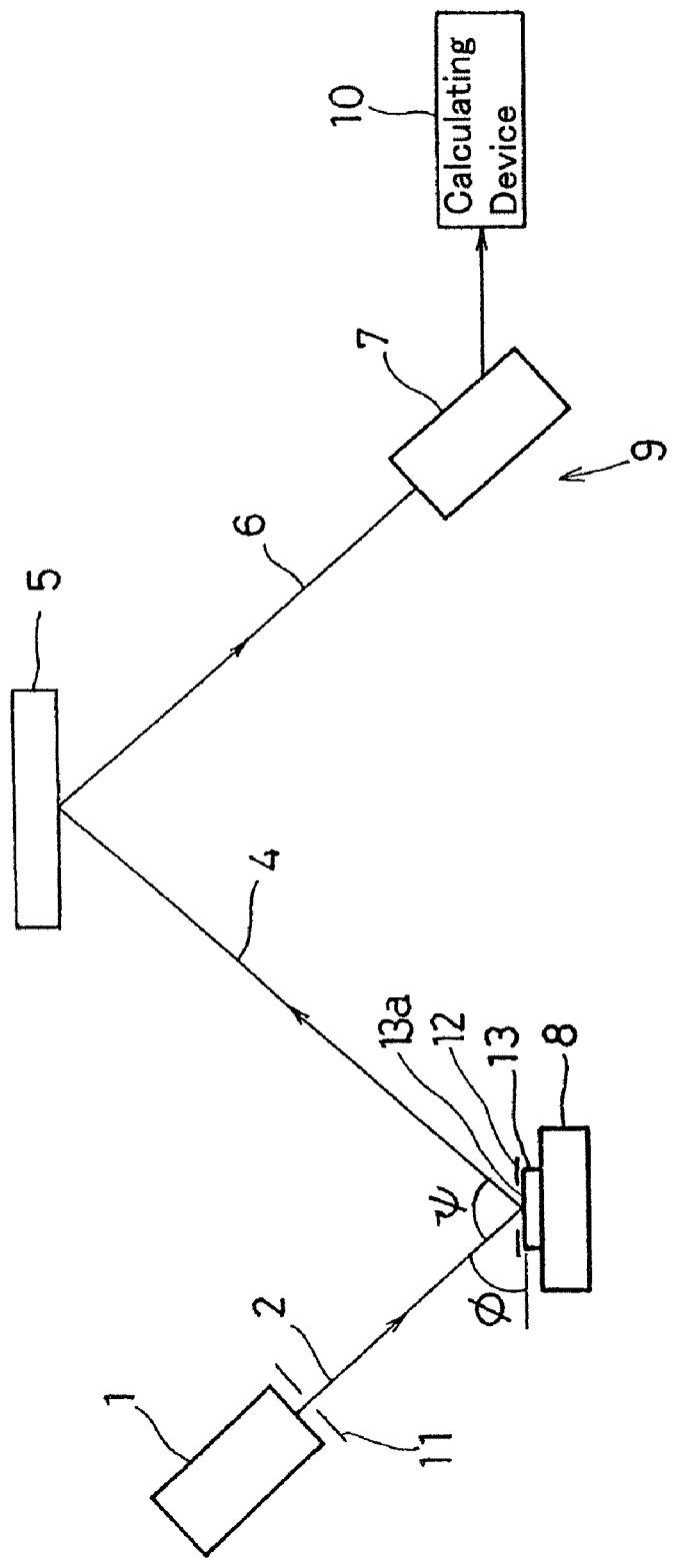
FIG. 1 is a schematic diagram showing an X-ray fluorescence spectrometer according to a preferred embodiment of the present invention.

Hereinafter, an X-ray fluorescence spectrometer according to a preferred embodiment of the present invention will be described with particular reference to the accompanying drawings. As shown in FIG. 1, the X-ray fluorescence spectrometer includes a sample stage 8 for the support of a sample 13 thereon, an X-ray source 1 such as, for example, an X-ray tube for irradiating primary X-rays 2 towards the sample 13, and a detecting device 9 for measuring the intensity of secondary X-rays 4 such as, for example, fluorescent X-rays and scattered X-rays emanating from the sample 13. An aperture 11 is disposed forwardly of the X-ray source 1, and the divergence of primary X-rays 2 is determined by an opening of the aperture 11. Also, a mask 12 is disposed immediately above a surface 13a of the sample 13, and a radiation area of the sample surface 13a, which is irradiated with primary X-rays 2, is determined by an opening of the mask 12. The detecting device 9 includes a spectroscopic device 5 for monochromating the secondary X-rays 4 emanated from the sample 13, and a detector 7 for measuring the intensity of each of monochromated secondary X-rays 6. It is to be noted that without using the spectroscopic device 5, a detector having a high energy resolving power may be used as the detecting device.

And included is a calculating device 10, which is operable to calculate the theoretical intensity of the secondary X-rays 4, emanated from each of elements contained in the sample 13, on the basis of the assumed composition, that is, the assumed concentrations of elements, and then to successively approximately modify and calculate the assumed composition so that the calculated theoretical intensity and the converted and measured intensity, which has been detected by the detecting device 9 and then converted in a theoretical intensity scale, can match with each other, to thereby calculate the concentrations of the elements contained in the sample 13, that is, the composition of the sample 13, which calculating device 10, when calculating the theoretical intensity, performs a simulation to determine the theoretical intensity of the secondary X-rays 6 for each of optical paths (2, 4, 6), using the size of the sample 13, the intensity and the incident angle $\phi$ of primary X-rays 2 impinged upon various areas of the sample surface 13a as parameters.

Also, as far as elements such as, for example, oxygen and carbon, of which fluorescent X-rays can not be measured such as disclosed in the Japanese Patent Application No. 2004-251785 (Japanese Laid-open Patent Publication No. 2006-071311), (i.e., the fluorescent X-rays of those elements cannot be substantially measured because the intensity is low and a considerable decay occurs as a result of absorption. Those elements are hereinafter referred to as "unmeasured elements"), the calculating device 10 employed in this embodiment assumes an average atomic number and successively approximately modifies and calculates the assumed average atomic number with the use of scattered X-rays 4 as the corresponding secondary X-rays so that the theoretical intensity and the converted and measured intensity can match with each other.

For the theoretical and measured intensities of the scattered X-rays referred to above one selected from the group consisting of the theoretical and measured intensities of the scattered X-rays of continuous X-rays of primary X-rays, the theoretical and measured intensities of Thomson scattered X-rays, and ratios of the theoretical and measured intensities of two of those scattered X-rays may be used.

The X-ray fluorescence spectrometer of the present invention operates in the following manner. The sample 13 placed on the sample stage 8 is irradiated with primary X-rays 2 emanated by the X-ray source 1, secondary X-rays 4 emanating from the sample 13 are allowed to be incident upon the spectroscopic device 5, and the intensity thereof is measured by the detector 7 for each of secondary X-rays 6 so monochromated. And, the calculating device 10 performs a calculation according to such a flowchart shown in FIG. 2.

At the outset, and at Step 1, an initial value of the concentration of each measured element, an initial value of the average atomic number of the unmeasured elements and, if required, an initial value of the area density (or thickness) of the sample are set. The initial value of the concentration of each measured element can be set depending on the category of the sample, but may all be set to 1 mass %. The initial value of the average atomic number of the unmeasured elements is set to, for example, 8.

At subsequent Step 2, the measured intensities $I_{measM}$ of fluorescent X-rays and scattered X-rays are converted into a theoretical intensity scale with the use of the following equation (1) to provide respective converted and measured intensities $I_{measT}$.

$$I_{measT} = A(I_{measM})^2 + BI_{measM} + C \quad (1)$$

Then at Step 3, based on the initial values so set, the theoretical intensity $I_{FTi}$ of each of the fluorescent X-rays and the theoretical intensity $I_{STi}$ of the scattered X-rays are calculated. While the features of the present invention lie in the manner of calculating the theoretical intensities at Steps 3 and 4, the details thereof will be described later.

At Step 4, the concentration of each of the measured elements and the average atomic number of the unmeasured elements are changed by a predetermined respective value and the theoretical intensities after such change are calculated. In other words, with respect to the fluorescent X-rays, the theoretical intensity $I_{FTi}^j$ of the i element, when the concentration of the j element is changed by dw %, and the theoretical intensity $I_{FTi}^z$, when the average atomic number of the unmeasured elements is changed by dZ, are calculated, and with respect to the scattered X-rays, the theoretical intensity $I_{STi}^j$ of the i scattered X-rays, when the concentration of the j element is changed by dw %, and the theoretical intensity $I_{STi}^z$ of the i scattered X-rays, when the average atomic number of the unmeasured elements is changed by dZ, are calculated. The parameters dZ referred to above is chosen to be, for example, 0.05.

At Step 5, based on the difference equation, the concentration of each measured element and the average atomic number of the unmeasured elements are updated. More specifically, the following simultaneous difference equations (2) and (3) are formulated for the fluorescent X-rays and the scattered X-rays, respectively, and those simultaneous difference equations are solved to determine modification values $\Delta wj$ and $\Delta Z$ for updating the concentration of each measured element and the average atomic number of the unmeasured elements.

$$I_{fmeasTi} - I_{FTi} = (dI_{FTi}/dZ)\Delta Z + \Sigma(dI_{FTi}/dwj)\Delta wj \quad (2)$$

$$I_{smeasTi} - I_{STi} = (dI_{STi}/dZ)\Delta Z + \Sigma(dI_{STi}/dwj)\Delta wj \quad (3)$$

It is to be noted that with respect to the fluorescent X-rays, each of the differential terms is determined by the following equation (4).

$$(dI_{FTi}/dwj) = ((I_{FTi}^j - I_{FTi}^j)/dwj) \quad (4)$$

With respect to the scattered X-rays, where the intensity of, for example, Compton scattered X-rays or Thomson scattered X-rays is solely used for the intensity of the scattered X-rays, each of the differential terms is determined by the following equation (5) in a manner similar to that of the fluorescent X-rays.

$$(dI_{STi}/dwj) = ((I_{STi}^j - I_{STi})/dwj) \quad (5)$$

For the intensity of the scattered X-rays, where the intensity ratio of, for example, the Compton scattered X-rays and the Thomson scattered X-rays is used, the intensity ratio of them is applied where the intensity of the sole scattered X-rays is used. By way of example, the ratio of the theoretical intensity $I_{STiComp}$ of the Compton scattered X-rays relative to the theoretical intensity $I_{STiThom}$ of the Thomson scattered X-rays is applied as the theoretical intensity ratio $I_{STiR}$ of the scattered X-rays to the theoretical intensity $I_{STi}$ of the scattered X-rays in each of the equations (3) and (5) above as shown in the following equation (6).

$$I_{STiR} = (I_{STiComp}/I_{STiThom}) \quad (6)$$

Similarly, the intensity ratio of the scattered X-rays is equally applied to the converted and measured intensity $I_{smeasMi}$ of the scattered X-rays in the equation (3) above, the measured intensity $I_{measM}$ of the scattered X-rays in the equation (1) above and at Step 6 as will be described later.

By solving the simultaneous difference equations (2) and (3) so formulated, determining the modification values $\Delta wj$ and $\Delta Z$ for the concentration of each measured element and the average atomic number Z of the unmeasured elements and adding to the initial values $wi_{old}$ and $Z_{old}$ as shown in the following equations (7) and (8), the updated values $wi_{new}$ and $Z_{new}$ are determined. The concentration for the unmeasured elements is determined by subtracting the sum of the respective concentrations wi of the measured elements from 100%.

$$wi_{new} = wi_{old} + \Delta wj \quad (7)$$

$$Z_{new} = Z_{old} + \Delta Z \quad (8)$$

Thereafter and at Step 6, based on the updated concentration $wi_{new}$ of each of the measured elements and the average atomic number $Z_{new}$ of the unmeasured elements, the theoretical intensity $I_{FTi}$ of each of the fluorescent X-rays and the theoretical intensity $I_{STi}$ of the scattered X-rays are calculated and depending on whether or not the difference between it and the converted and measured intensity $I_{measT}$ determined by the equation (1) above is not bigger than a predetermined value, a convergence test is carried out. The convergence test may be carried out depending on whether or not the difference between the theoretical intensity and the converted and measured intensity is not higher than a predetermined ratio (for example, 0.1%) of the converted and measured intensity. If determination is made that no convergence take place, the program flow returns to Step 4, repeating the flow from Step 4 to Step 6 until the convergence takes place. In other words, with respect to the secondary X-rays emanating from the sample (the fluorescent X-rays of the measured element and the scattered X-rays corresponding to the unmeasured elements), so that the theoretical intensity and the converted and measured intensity may match with each other, the assumed concentration of the measured element and the assumed average atomic number of the unmeasured elements are successively approximately modified and calculated.

And, if determination is made that the convergence takes place, the program flow goes to Step 7, at which the recent concentration of each measured element, the average atomic number of the unmeasured elements and, if required, the area density (or thickness) of the sample are outputted as a result.

It is to be noted that the previously described Step 5 may be divided into the following Steps 5A and 5B. In the first place, at Step 5A, only the concentration of each of the measured elements is updated while the average atomic number of the unmeasured elements is fixed. Then at Step 5B, while the concentration of each of the measured elements is fixed to the updated value, $\Delta Z$ is determined using the following equation (9) and only the average atomic number of the unmeasured elements is updated.

$$I_{smeasTi} - I_{STi} = (dI_{STi}/dZ)\Delta Z \quad (9)$$

Also, when the area density is analyzed simultaneously, one scattered X-rays to be measured is added and not only is the equation (3) referred to previously added with respect to such scattered X-rays, but a differential term representative of the area density has to be added to the right hand of each of the simultaneous difference equations (2) and (3). By way of example, the equation (3) referred to previously will be two equations, one associated with the Compton scattered X-rays and the other with the Thomson scattered X-rays.

Figure 2:
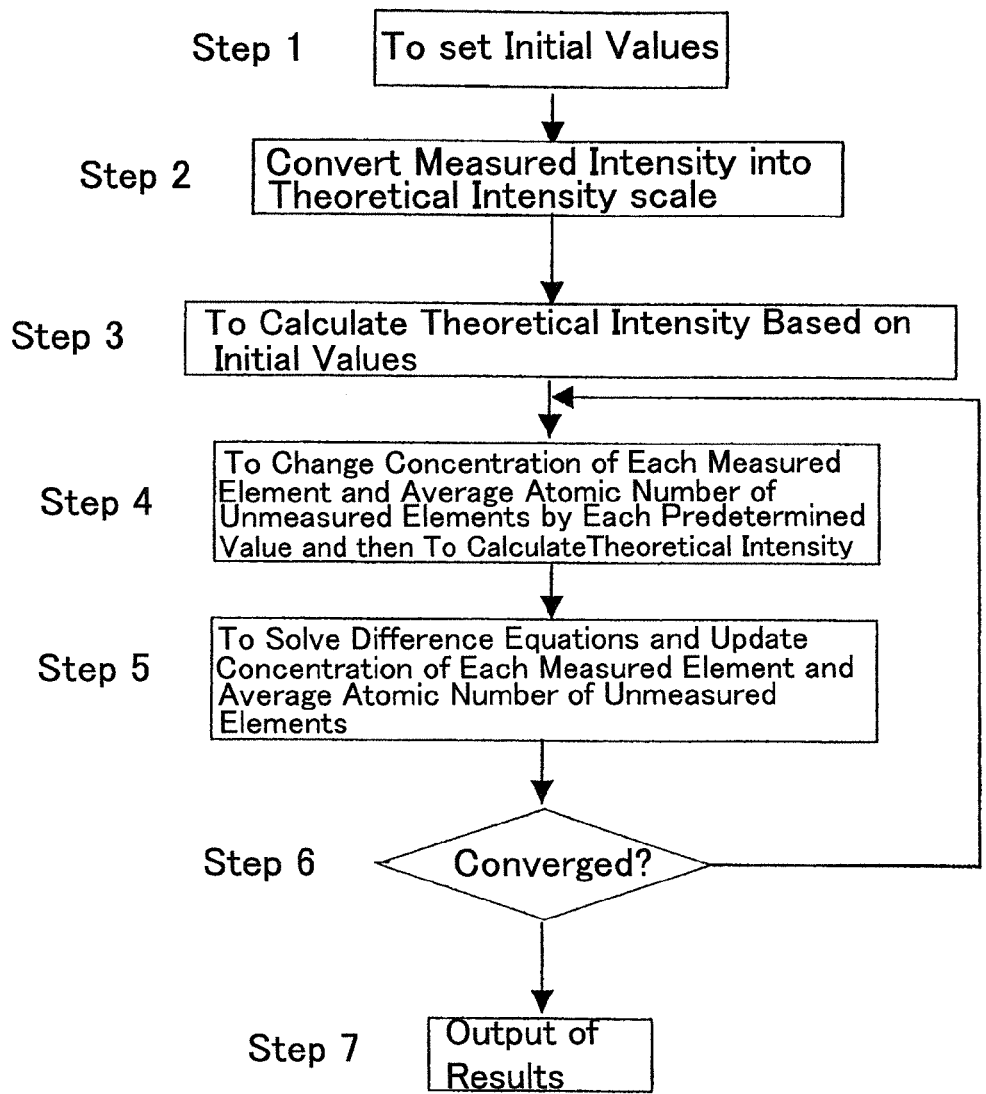
FIG. 2 is a flowchart showing the sequence of computation performed by a calculating device employed in the X-ray fluorescence spectrometer.

It is to be noted that in place of the flowchart shown in FIG. 2, the calculating device 10 may perform the calculation according to a method known as a solution to the nonlinear problems, such as, for example, a marcato method, a simulated annealing method or a genetic algorithm.

Selection of the intensity of the scattered X-rays according to the sample is similar to that disclosed in the previously mentioned Patent Application No. 2004-251785 (Japanese Laid-open Patent Publication No. 2006-071311). Dividing the unmeasured elements into hydrogen and elements other than hydrogen, assuming the average atomic number with respect to the unmeasured elements other than hydrogen and utilizing both of the intensity of the Compton scattered X-rays and the Thomson scattered X-rays are all similar to those disclosed. In addition, in the foregoing, in place of the Compton scattered X-rays, utilization of scattered X-rays of continuous X-rays of primary X-rays (background) is also similar to that disclosed.

Figure 3:
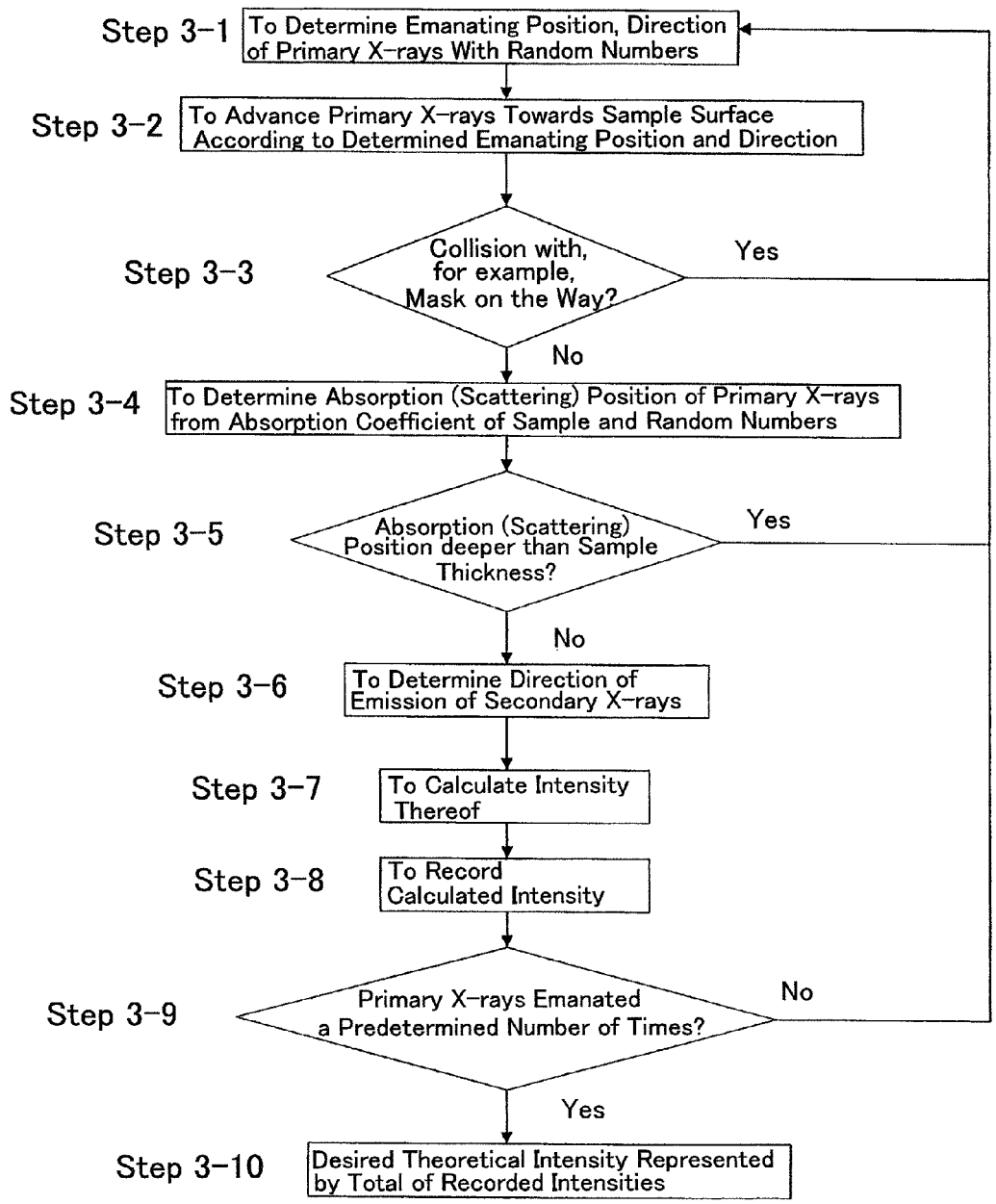
FIG. 3 is a flowchart showing the sequence of computation of the theoretical intensity performed by the calculating device.

In the next place, calculation of the theoretical intensity at each of Steps 3 and 4, which form respective features of the present invention, will be described in detail. In calculating the theoretical intensity, the calculating device 10 employed in the X-ray fluorescence spectrometer according to this embodiment performs a simulation to calculate the theoretical intensity of the secondary X-rays for each of optical paths (2, 4, 6), using the size of the sample 13, the intensity and the incident angle $\phi$ of primary X-rays 2 impinged upon various areas of the sample surface 13a as parameters. More specifically, the theoretical intensity is calculated in the following manner according to such a flowchart as shown in FIG. 3.

In the first place, at Step 3-1, the emanating position and direction of primary X-rays are determined with random numbers.

Then at Step 3-2, in accordance with the emanating position and direction so determined, primary X-rays are advanced to the sample surface.

Thereafter, at Step 3-3, a decision is made to determine whether or not the advanced primary X-rays during the course of advancement impinge upon the aperture 11 or the mask 12. If the impingement occurs, the program flow returns to Step 3-1, but if no impingement occur, the program flow goes to Step 3-4.

At Step 3-4, from the absorption coefficient of the sample and random numbers, the absorption (scattering) position of primary X-rays is determined.

At the following Step 3-5, a decision is made to determine whether or not the determined absorption (scattering) position is deeper than the thickness of the sample. If it is deeper, the program flow returns to Step 3-1, but if it is not, the program flow goes to Step 3-6.

At Step 3-6, the direction of emission of the secondary X-rays (fluorescent X-rays or scattered X-rays) that are emanated as a result of absorption (scattering) of primary X-rays thereof is determined.

Then, at Step 3-7, the intensity of the secondary X-rays, of which direction of emission has been determined, is calculated and the intensity so calculated is recorded at Step 3-8.

Then at Step 3-9, a decision is made to determine whether or not primary X-rays should be emanated a number of times that is preset ahead of time. Where they are not emanated, the program flow returns to Step 3-1, but where they are emanated, the program flow goes to Step 3-10.

Finally at Step 3-10, the total of the intensities recorded at Step 3-8 will come to represent the theoretical intensity that are sought.

It is to be noted that the contents executed from Step 3-1 to Step 3-3 can be calculated ahead of time since it does not rely on the sample. In such case, the emanating position and direction of primary X-rays at the sample surface for each trial are calculated for a predetermined number of times and stored. Then, at the time of calculation to be done to the actual sample, a step of successively invoking the emanating position and direction of primary X-rays stored is employed in place of the flow from Step 3-1 to Step 3-3. In addition, at each trial of calculation that is carried out ahead of time, the random numbers that are used at Step 3-4 may be emanated simultaneously and may be stored together with the emanating position and direction of primary X-rays. By so doing, emanation of the random numbers, which requires a relatively long time, need not be carried out during the actual calculation for each sample, resulting in reduction in length of time required to accomplish the calculation.

As hereinbefore described, according to the X-ray fluorescence spectrometer, since in calculating the theoretical intensity, the simulated calculation to determine the theoretical intensity of the secondary X-rays 6 for each optical path (2, 4, 6) (which calculation may be also called a ray tracing calculation or a beam tracking method) is carried out using the size of the sample 13, the incident angle $\phi$ and the intensity of primary X-rays 2 impinged upon various position of the sample surface 13a as parameters, there is no need to prepare a plurality of sensitivity curves ahead of time and, with respect to various samples 13, the theoretical intensity can be calculated conveniently with the geometry effect sufficiently taken into consideration in conformity with the reality and the samples 13 can be quantitatively analyzed sufficiently accurately. It is to be noted that the total length of time required to calculate the composition of the sample may be prolonged as compared with that in the conventional case, but can fall within the practically sufficient range.

It is also to be noted that during the flow from Step 1 to Step 4, the calculating device 10 preferably has a capability of simultaneously calculating the theoretical intensity with respect to a plurality of assumed compositions. According to this preferred construction, the total length of time required to accomplish the calculation can be reduced.

Also, the calculating device 10 preferably makes use of a distribution of angles of incidence $\phi$ of primary X-rays or angles of scattering $\psi$ at the sample surface, which has been predetermined ahead of time. Those distributions are of a kind in which the detection efficiency exhibited by the spectroscopic device 5 is taken into consideration. Since the distributions of the incident angles $\phi$ and the scattering angles $\psi$ at the sample surface do not generally change unless the X-ray source 1 is changed and, accordingly, in a preferred construction, they are predetermined ahead of time and are then used in calculating the theoretical intensity. According to this, since the length of time required to accomplish the calculation of the theoretical intensity, the total length of time in accomplishing the calculation can also be reduced. In particular, it is effective where the sample 13 is thin such as represented by a thin film. It is to be noted that since the distributions of the incident angles $\phi$ and the scattering angles $\psi$ at the sample surface do not generally change with change of the sample, there is no need to prepare a number of distributions such as a number of sensitivity curves required in the conventional art.

Figure 4:
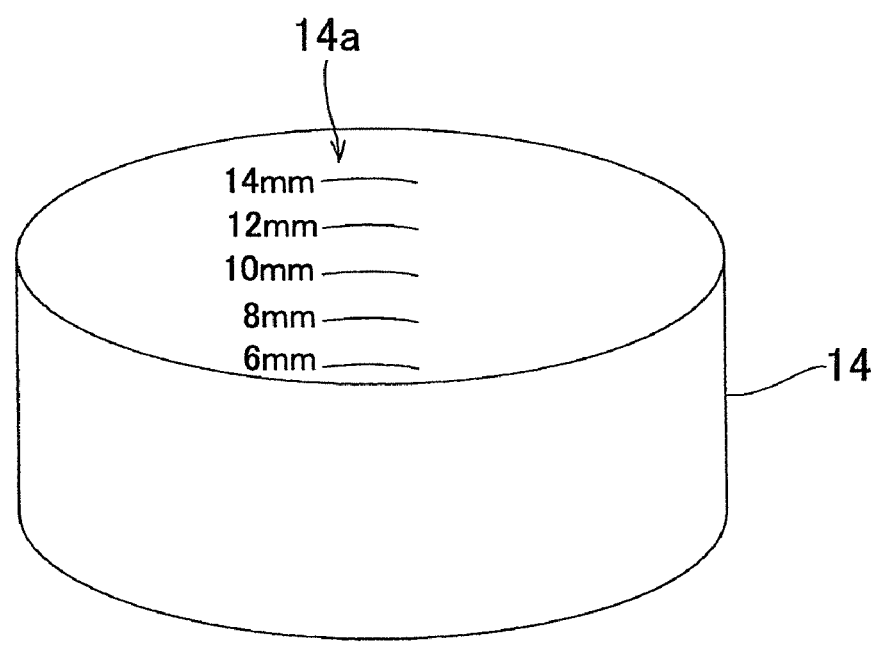
FIG. 4 is a perspective view showing a sample container employed in the X-ray fluorescence spectrometer.

Further, preferred is the provision of a sample container 14 having a scale 14a that is used to measure the height of the sample surface such as shown in FIG. 4. By way of example, something like a pot of a rice cooker having a scale formed in an inner surface thereof may be used. Referring to FIG. 1, the incident angle $\phi$ and the intensity of primary X-rays 2 irradiated on each position of the sample surface 13a as the parameter referred to previously changes with the height of the sample surface 13a relative to the X-ray source 1 and, therefore, the height of the sample surface 13a must be known. In this preferred construction, since the sample container 14 is provided with the scale 14a for measuring the height of the sample surface 13a, measurement and adjustment of the height of the sample surface 13a can be easily accomplished.

The X-ray fluorescence spectrometer according to the foregoing embodiment is normally provided with a computer and, hence, a program for causing the computer to function as the previously described calculating device is also another preferred embodiment of the present invention.

What is claimed is:

1. An X-ray fluorescence spectrometer which comprises:
   an X-ray source for irradiating primary X-rays towards a sample;
   a detecting device for measuring an intensity of secondary X-rays emanating from the sample; and
   a calculating device operable to calculate a theoretical intensity of simulated secondary X-rays, emanated from an element or elements contained in the sample, based on an assumed composition and then to successively approximately modify and calculate the assumed composition so that the theoretical intensity and the measured intensity, which has been detected by the detecting device and then converted into a theoretical intensity scale, match with each other, to thereby calculate a composition of the sample;
   wherein the calculating device, when calculating the theoretical intensity, simulates simulated primary X-rays emanating from different positions and different directions which are determined with random numbers, respectively, to thereby determine the theoretical intensity of the simulated secondary X-rays using a plurality of optical paths through which the simulated primary X-rays travel towards a surface of the sample, and using a size of the sample, and an intensity and a plurality of incident angles of the simulated primary X-rays impinged upon various areas of the sample surface as parameters.

2. The X-ray fluorescence spectrometer as claimed in claim 1, wherein with respect to a plurality of assumed compositions, the calculating device calculates the theoretical intensity simultaneously.

3. The X-ray fluorescence spectrometer as claimed in claim 1, wherein the calculating device makes use of a distribution of incident angles or a distribution of scattering angles of the simulated primary X-rays on the sample surface, which has been predetermined ahead of time.

4. The X-ray fluorescence spectrometer as claimed in claim 1, further comprising a sample container provided with a scale for measuring a height of the sample surface.

5. A tangible computer-readable medium containing a program for enabling a computer, which is provided with the X-ray fluorescence spectrometer as defined in claim 1, to function as the calculating device.

* * * * *